(12) United States Patent
Vaughan et al.

(10) Patent No.: US 11,547,610 B2
(45) Date of Patent: Jan. 10, 2023

(54) TYMPANOSTOMY TUBE AND A PLACEMENT DEVICE

(71) Applicant: AVENTAMED DESIGNATED ACTIVITY COMPANY, Cork (IE)

(72) Inventors: John Vaughan, Cork (IE); Olive O'Driscoll, Kinsale (IE); Carol Grimes, Skerries (IE)

(73) Assignee: Aventamed Designated Activity Company, Cork (IE)

(*) Notice: Subject to any disclaimer, the term of this patent is extended or adjusted under 35 U.S.C. 154(b) by 394 days.

(21) Appl. No.: 16/757,548

(22) PCT Filed: Nov. 2, 2018

(86) PCT No.: PCT/EP2018/080015
§ 371 (c)(1),
(2) Date: Apr. 20, 2020

(87) PCT Pub. No.: WO2019/086608
PCT Pub. Date: May 9, 2019

(65) Prior Publication Data
US 2021/0169697 A1    Jun. 10, 2021

(30) Foreign Application Priority Data
Nov. 2, 2017  (EP) .................................... 17199754

(51) Int. Cl.
*A61F 11/20*    (2022.01)
(52) U.S. Cl.
CPC .................. *A61F 11/202* (2022.01)
(58) Field of Classification Search
CPC ................. A61F 11/202; A61B 17/3468
See application file for complete search history.

(56) References Cited

U.S. PATENT DOCUMENTS

| | | | | |
|---|---|---|---|---|
| 4,744,792 A | * | 5/1988 | Sander | A61F 11/202 623/10 |
| 5,207,685 A | * | 5/1993 | Cinberg | A61F 11/202 606/1 |

(Continued)

FOREIGN PATENT DOCUMENTS

| | | |
|---|---|---|
| FR | 2950526 B1 | 12/2012 |
| GB | 2204796 A | 11/1988 |

(Continued)

OTHER PUBLICATIONS

International Search Report issued in PCT/EP2018/080015; dated Feb. 12, 2019.

*Primary Examiner* — Richard G Louis
(74) *Attorney, Agent, or Firm* — Studebaker & Brackett PC

(57) ABSTRACT

A tympanostomy tube placement device has a stem with a needle having a tip configured to pierce a tympanic membrane. A retainer is on the needle and includes four fingers extending axially at a distance from said axis and at 90° circumferential separations in one example. The retainer is movable from a distal position at which it presses radially inwardly against the tube distal flange tabs to retain the distal flange in a folded position, to a proximal position at which the tube distal flange is free to spring out radially to a deployed position. The retainer fingers extend through tube proximal flange passageways and press the tube distal flange inwardly, while leaving a distally-facing face of the proximal flange exposed radially outwardly of the retainer. Hence, the proximal flange has its final deployed configuration throughout, and so can act as a physical stop member against the tympanic membrane and also provides visualisation for the surgeon because it extends radially outwardly of the stem.

20 Claims, 9 Drawing Sheets

(56) References Cited

U.S. PATENT DOCUMENTS

| | | | | |
|---|---|---|---|---|
| 5,246,455 A | * | 9/1993 | Shikani | A61F 11/202 623/10 |
| 5,466,239 A | * | 11/1995 | Cinberg | A61F 11/202 606/1 |
| 2003/0187456 A1 | * | 10/2003 | Perry | A61F 11/202 606/109 |
| 2009/0209972 A1 | | 8/2009 | Loushin et al. | |
| 2009/0299379 A1 | * | 12/2009 | Katz | A61F 11/202 606/109 |
| 2012/0150119 A1 | * | 6/2012 | Schaeffer | A61M 27/002 604/164.11 |
| 2015/0164695 A1 | * | 6/2015 | Liu | A61B 17/3478 606/109 |

FOREIGN PATENT DOCUMENTS

| | | |
|---|---|---|
| GB | 2437708 A | 11/2007 |
| WO | 2011/008948 A1 | 1/2011 |
| WO | 2013/113022 A1 | 8/2013 |
| WO | 2013/155169 A1 | 10/2013 |

\* cited by examiner

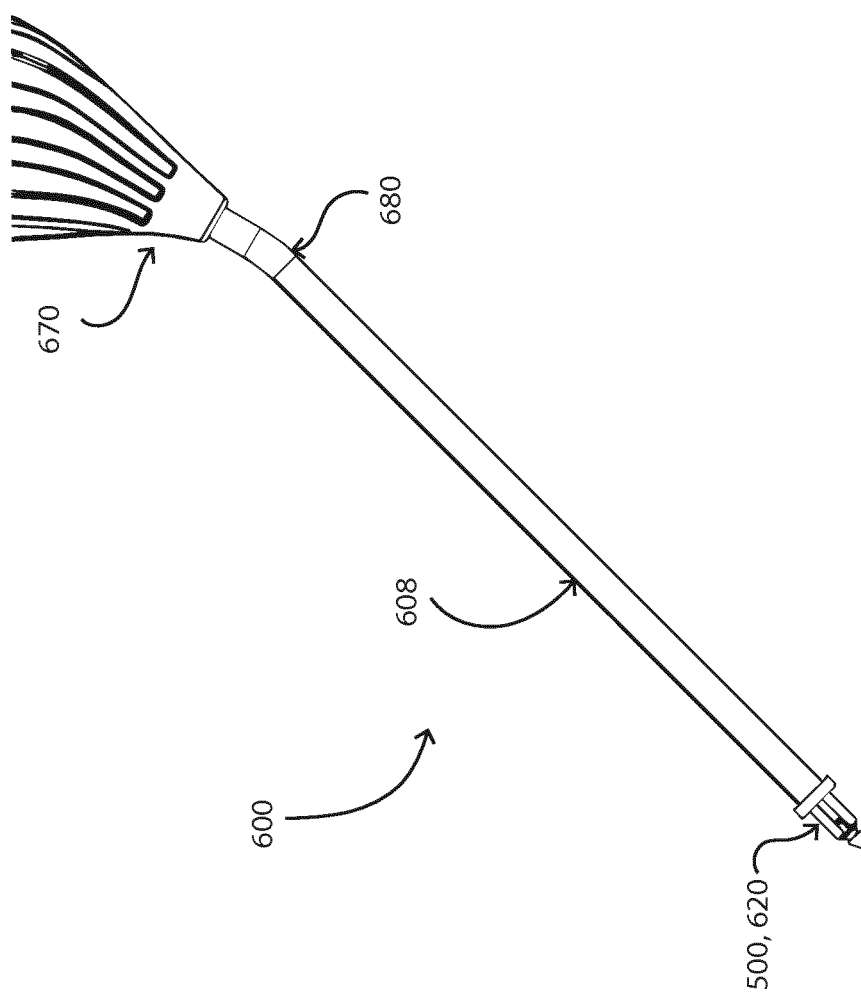

TYMPANOSTOMY TUBE AND A PLACEMENT DEVICE

INTRODUCTION

Field of the Invention

The invention relates to tympanostomy tubes and placement devices.

Prior Art Discussion

When patients are treated surgically for conditions in the ear, for example Otitis Media, they are typically treated by a tympanostomy tube being placed for ventilation. A tympanostomy tube is a small tube which is placed in the tympanic membrane (or "ear drum") manually by a surgeon, typically under general anesthetic in an operating theatre. The surgeon cleans wax from the ear canal, makes a small incision in the tympanic membrane, uses suction to remove any fluid in the middle ear, and then positions the tube in the tympanic membrane. The tube equalizes the pressure between the middle and outer ear and ventilates the middle ear space. Tympanostomy tube placement is the most common reason why children undergo surgery with a general anesthetic.

At present, when it is desired to place a tympanostomy tube, it is typically done manually because the inner flange needs to be particularly wide to stay in the tympanic membrane for an extended period of time. The tympanostomy tube sometimes requires a lead-in feature on the inner flange of the tube to aid insertion of the manual placement using current ENT instrumentation.

A placement device allows tympanostomy tubes to be placed safely and quickly in a clinical setting, allowing tubes to be placed without the need for general anaesthesia in all patients.

WO2013/155169 (Acclarent) and U.S. Pat. No. 4,744,792 (Richards Medical Co.) describe tympanostomy tubes.

WO2011/008948 (Acclarent) describes a tympanostomy tube and a placement device wherein the tip creates an incision in the tympanic membrane and ejects a tympanostomy tube into the membrane. A tympanostomy tube is restrained by sleeves surrounding it so that its flanges lie axially. The sleeves are withdrawn during deployment to allow the flanges to un-fold to the radial position.

WO2013/113022 (Entra Tympanic LLC) describes a placement and removal device which has vacuum channels to immobilize the membrane during the tube placement. In this case the tube's flanges are not folded, the tube retaining the same physical configuration throughout.

The invention is directed towards providing a placement device for effective deployment of a tube, especially a tube having a wide distal flange for a long dwell time or "time to extrusion". The time to extrusion is dependent on the clinical requirement of the patient.

SUMMARY OF THE INVENTION

A tympanostomy tube placement device has a stem with a needle having a tip configured to pierce a tympanic membrane. A retainer is on the needle and comprises fingers extending axially at a distance from said axis and equal circumferential separations in one example. The retainer is movable from a distal position at which it presses radially inwardly against the tube distal flange tabs to retain the distal flange in a folded position, to a proximal position at which the tube distal flange is free to spring out radially to a deployed position. The retainer fingers extend through tube proximal flange passageways and press the tube distal flange inwardly, while leaving a distally-facing face of the proximal flange exposed radially outwardly of the retainer. Hence, the proximal flange has its final deployed configuration throughout, and so can act as a physical stop member against the tympanic membrane and also provides visualisation for the surgeon because it extends radially outwardly of the stem.

In various aspects we describe a tympanostomy tube placement device comprising:
  a stem connected to a deployment mechanism or having a coupler for connection to a deployment mechanism;
  a needle having a tip configured to pierce a tympanic membrane, the needle having a longitudinal axis; and
  a retainer comprising a plurality of fingers extending axially at a distance from said longitudinal axis;
  wherein the retainer is movable from a pre-deployment distal position at which it is adapted to press radially inwardly against a tube distal flange to retain said distal flange in a folded position, to a deployment proximal position at which a tube distal flange is free to spring out radially to a deployed position.

Preferably, there are at least two diametrically opposed retainer fingers. Preferably, the fingers have an arcuate cross-sectional shape with a concave internal surface.

The device may further comprise a handle connected to the stem, and the stem may be rotatable with respect to the handle, and there may be a user actuator for rotation of the stem. Preferably, the needle is lockable in the stem so that it rotates with the stem. Preferably, the needle comprises a lock member for engagement within a recess of the stem. Preferably, the stem is cranked or bent along its length.

Preferably, the placement device further comprises:
  a tympanostomy tube comprising a proximal flange, an inter-lumen connector, and a distal flange, and in which the proximal flange comprises passageways; and in which
  in a pre-deployment position the retainer fingers extend through the proximal flange passageways and press the tube distal flange inwardly.

Preferably, the tube distal flange comprises at least one tab aligned in circumferential position with a retainer finger and being pressed inwardly by said finger in the pre-deployed position.

Preferably, the distal flange comprises a plurality of tabs. Preferably, the tabs are substantially equally circumferentially spaced. There may for example be four tabs, spaced apart by approximately 90°. Preferably, the passageways are through holes, each having a surface facing radially inwardly and engaging an outer surface of a retainer finger. Preferably, at least one through hole has an arcuate shape and said surface is concave. There may be at least one pair of diametrically opposed passageways.

The tube proximal flange may be of a first material and the distal flange may be of a second material, and said first material is more rigid than the second material.

Preferably, the retainer or the needle comprises an axial guide member configured to fit in the lumen of the tube pre-deployment.

The needle may comprise a recess proximally of the tip and configured to receive a folded-down part of a tab of a tube distal flange. Preferably, the recess (650) is annular. Preferably, the needle and the tube distal flange tabs are configured to form an arrow shaped formation when the distal flange is folded down.

In another aspect, we describe a tympanostomy tube comprising a proximal flange, an inter-flange connector with a lumen, and a distal flange, wherein the proximal flange comprises a plurality of axial through hole passageways and the distal flange is configured to be folded axially to a deployment position and to release radially to a deployed position.

Preferably, at least one passageway has a radially inner surface which is adjacent an external surface of the inter-flange connector. Preferably, said radially inner surface is curved. Preferably, the passageway has an arcuate shape with an outer concave surface facing radially inwardly. Preferably, there is at least one pair of diametrically opposed passageways. Preferably, the distal flange is more flexible than the proximal flange.

The proximal flange may be of a first material and the distal flange is of a second material, said first material being more rigid than the second material.

Preferably, the distal flange comprises a plurality of tabs at least one of which has a radial part extending in a direction which has a primarily radial component and a guide part extending in a direction which has a primarily axial component when the tube is relaxed, and the guide part is arranged to form a tapered configuration narrowing in the distal direction when the distal flange is pressed radially inwardly.

Additional Statements

We describe a tympanostomy tube comprising a proximal flange, an inter-flange connector with a lumen, and a distal flange, wherein the proximal flange comprises a plurality of axial passageways and the inner flange is configured to be folded axially to a deployment position and to release radially to a deployed position.

Preferably, the passageways have a radially inner surface which are adjacent an external surface of the inter-flange connector. Preferably, the passageways are through holes.

Preferably, the through holes have an arcuate shape with a concave surface facing radially inwardly. Preferably, there is at least one pair of diametrically opposed passageways.

The proximal flange may be of a first material and the distal flange is of a second material, and said first material is more rigid than the second material. The first material may be a metal, and the second material a polymer. The inter flange connector may be integral with the distal flange. The tube may be co-moulded of different materials.

We also describe a tympanostomy tube placement device comprising a stem connected to a deployment mechanism or having a coupler for connection to a deployment mechanism, and a needle having a tip configured to pierce a tympanic membrane, the needle having a longitudinal axis. The device may have a retainer comprising a plurality of fingers extending axially at a distance from said axis. The retainer may be movable from a distal position at which it is adapted to press radially inwardly against a tube distal flange to retain said distal flange in a folded position, to a proximal position at which a tube distal flange is free to spring out radially to a deployed position.

Preferably, there are at least two diametrically opposed retainer fingers, for example two pairs of opposed fingers.

Preferably, the fingers have an arcuate cross-sectional shape with a concave internal surface.

The device may further comprise a handle.

Preferably, the stem is rotatable with respect to the handle. Preferably, the device further comprises a user actuator for rotation of the stem.

Preferably, the needle is lockable in the stem so that it rotates with the stem. The needle may comprise a lock member for engagement within a recess of the stem.

Preferably, the stem is cranked or bent along its length.

We also describe a tympanostomy tube placement device further comprising a tube of any embodiment, with the retainer fingers extending through the tube proximal flange passageways and pressing the tube distal flange inwardly, while leaving a distally-facing face of the proximal flange exposed radially outwardly of the retainer. Such a device preferably has the tube factory-inserted in position so that the device is ready for use upon opening of its package. Preferably, the tube distal flange comprises a tab aligned in circumferential position with a retainer finger and being pressed inwardly by said finger.

DETAILED DESCRIPTION OF THE INVENTION

Brief Description of the Drawings

The invention will be more clearly understood from the following description of some embodiments thereof, given by way of example only with reference to the accompanying drawings in which:—

FIG. 18 is a perspective view of an alternative placement device, showing a stem which has a bend for good visibility during use.

DESCRIPTION OF THE EMBODIMENTS

Figure 1:
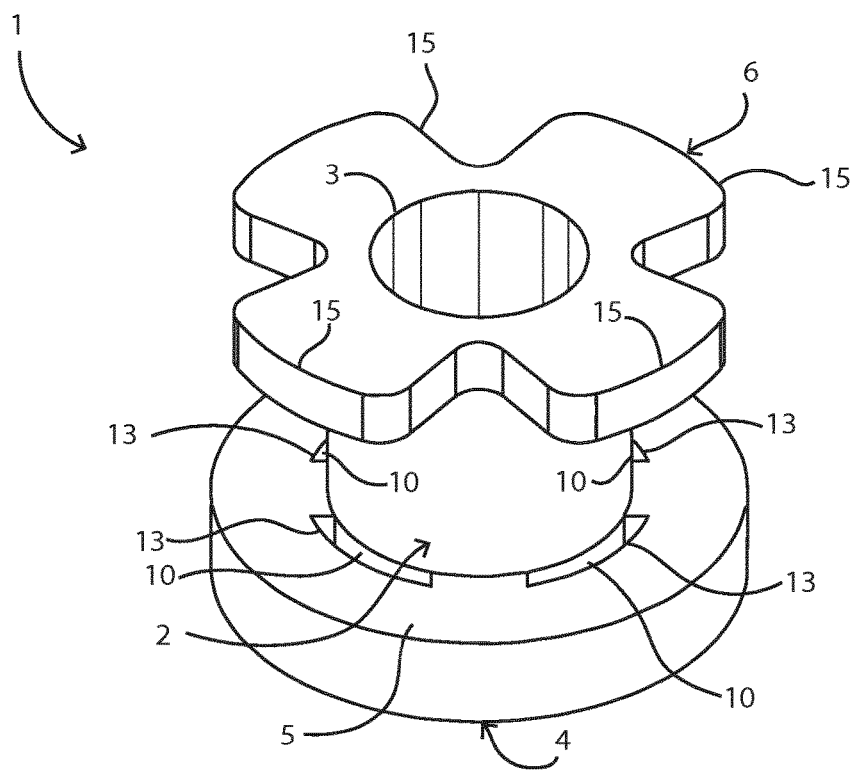
FIG. 1 is a perspective view of a tympanostomy tube.

Referring to FIG. 1 a tympanostomy tube 1 comprises an inter flange connector 2 with a lumen 3 for crossing through a tympanic membrane. The inter flange connector 2 connects an outer (proximal) flange 4 and an inner (distal) flange 6.

The proximal flange 4 is generally circular around its periphery, with an annular shape. It has a generally annular face 5 facing distally, towards the tympanic membrane in use.

The distal flange 6 is around the lumen 3 at its distal end and comprises four circumferentially spaced-apart tabs 15, at 90° to each other.

The proximal flange 4 includes four passageways, in this case arcuate through holes 10 around the periphery of the inter flange connector 2, and are equally spaced apart. The passageways 10 are axially and circumferentially aligned with the tabs 15 of the distal flange 6, being also at 90° to each other. Each passageway 10 has a radially-inwardly facing curved surface 13.

In various examples, the passageways are preferably through holes such as the passageways 10, and they preferably have an arcuate shape with a concave surface facing radially inwardly, as shown.

Figure 2:
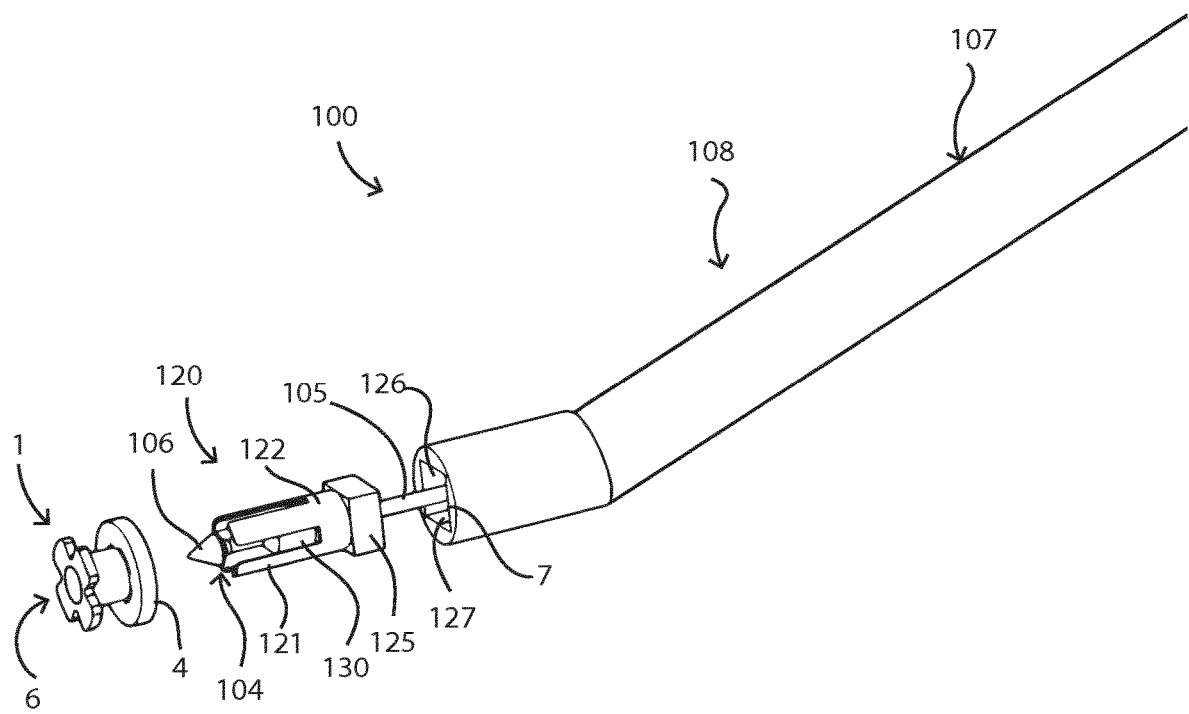
FIG. 2 is a perspective view showing a placement device for deployment of the tube.
Figure 3:
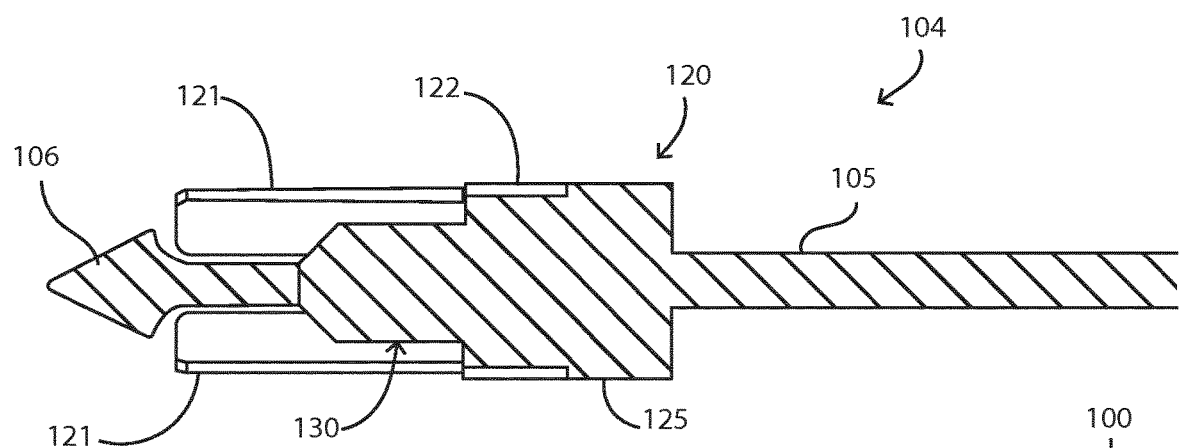
FIG. 3 is a longitudinal sectional view of a distal end of the device, showing particularly a needle and a retainer.

Referring to FIGS. 2 and 3 a placement device 100 comprises a needle 104 having a stem 105 and a tip 106. The needle 104 extends centrally through a sleeve 107 of a stem 108 of the device 100.

The needle stem 105 is in turn connected to a user-actuated deployment mechanism within a handle, not shown, proximally of the device stem 108. The mechanism is arranged to pull the needle 104 back in the proximal direction upon user pressing of an actuator button. This mechanism may be of any known type for user-actuated retraction, preferably spring-loaded for release of spring pressure to cause retraction.

FIG. 2 shows the tube 1 outside of the placement device 100, for clarity.

A retainer 120 is mounted to the needle 104 by connection to a central body 130 of the needle stem 105 by welding, or in other embodiments by a press-fit feature, or being integral, for example. The retainer 120 comprises four axially-extending fingers 121, equally spread circumferentially with 90° separations. The fingers are configured with cross-sectional shapes very slightly smaller than those of the tube passageways 10. They extend from a retainer base 122 on the needle stem and through the tube arcuate passageways 10 in use. A central guide 130 is also part of the needle 104, within the volume encompassed by the fingers 121. The retainer 120, specifically its fingers 121, is for holding the distal flange 6 axially for visualisation of the needle tip and to reduce the profile for insertion through the tympanic membrane in use, as described in more detail below with reference to FIGS. 3 to 7.

FIG. 3 shows more clearly the stem 105 and the tip 106 of the needle 104, with the central guide 130 within the retainer fingers 121. The retainer 120 is clearly illustrated, with the fingers 121 extending axially. The configuration of the central guide 130 allows it to fit within the lumen 3 of the tube 1 in use during placement. This provides a guiding effect for accurate location and movement of the fingers relative to the tube.

As shown in FIG. 2, the device stem sleeve 107 receives in its mouth 7 the retainer 120, the needle 104, and a lock member 125 which is an integral part of the needle 104. In use, it may be beneficial to rotate the sleeve 107 in order to improve the angular orientation of the stem in relation to the membrane. Due to the lock member 125 such rotation causes the needle 104 to rotate with the stem. The lock member 125 is of rectangular block shape for fitting into the sleeve mouth 7, also of rectangular cross-sectional shape. When this is engaged in the recess 7 it prevents the needle 104 and the attached retainer 120 from rotating. The angled or cranked stem sleeve 107, as shown in FIG. 2, is also to aid visualisation.

In other embodiments the locking of the needle to the stem may be by way of any other suitable feature such as a snap-fit fastener, possible in the configuration of a dimple for example.

Figure 4:
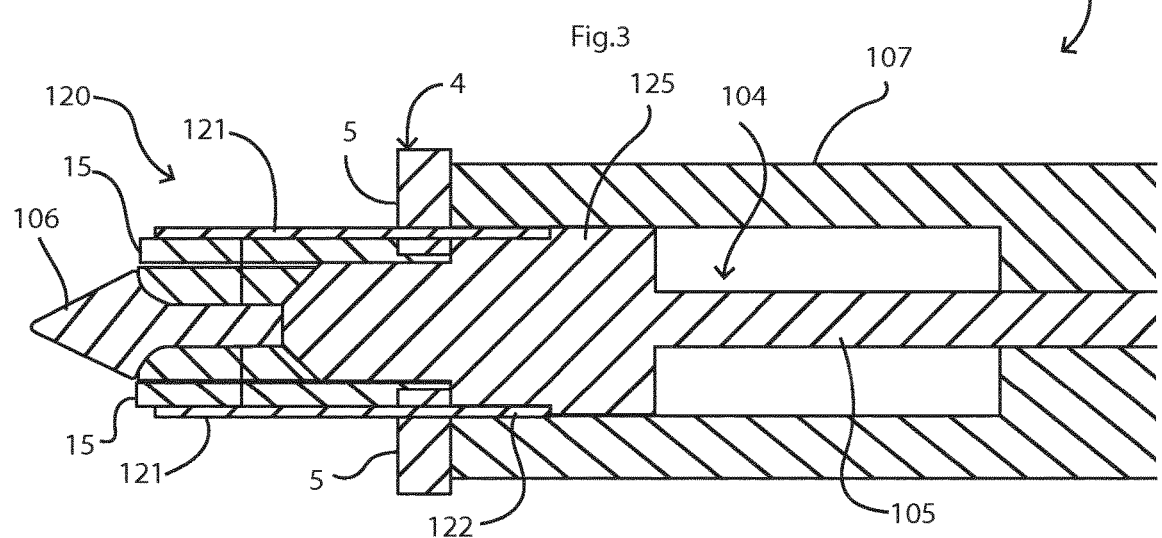
FIGS. 4, 5, and 6 are longitudinal sectional views showing operation of the placement device.
Figure 5:
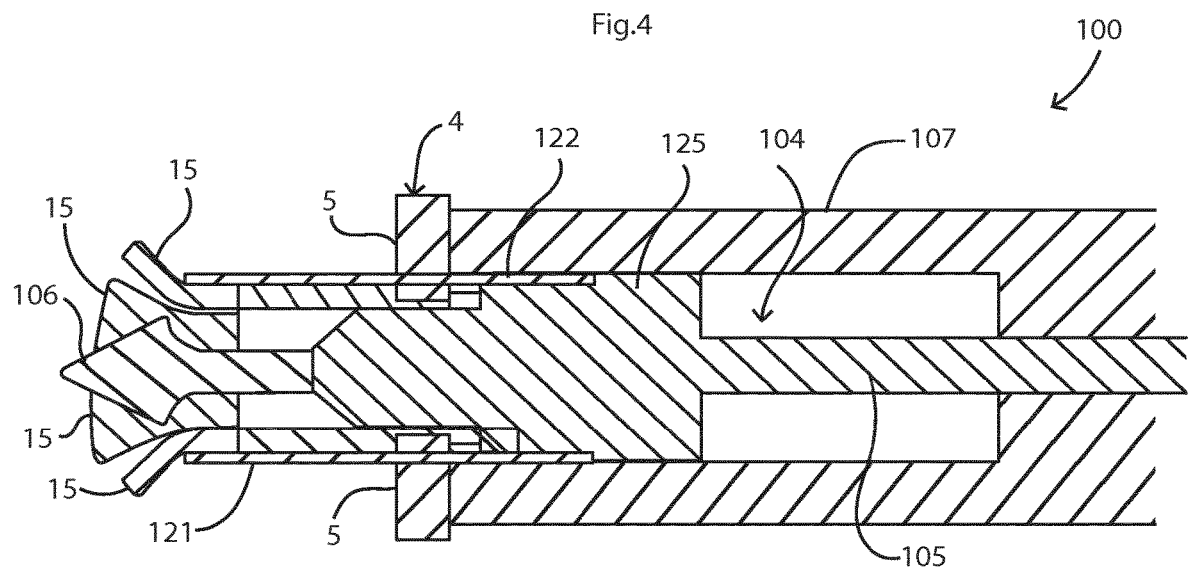
Figure 6:
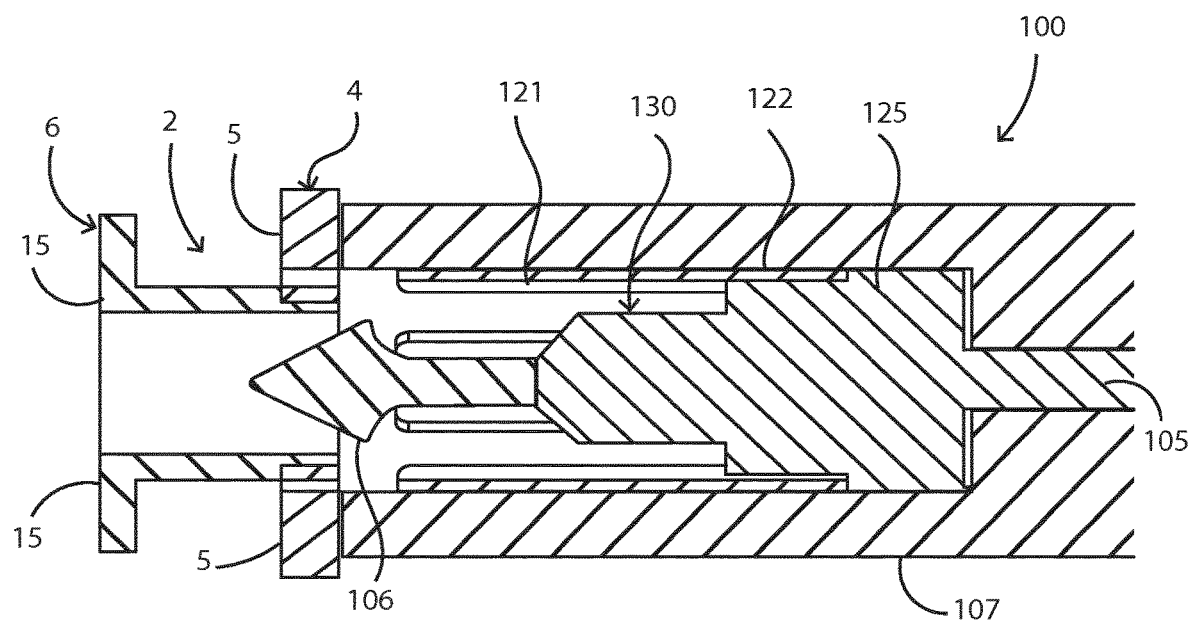

As is illustrated in FIGS. 4 to 6, before deployment, the retainer fingers 121 pass through the proximal flange 4, surround the inter-flange connector 2, and radially push in the (folded) distal flange 6. The fingers 121 radially push in the tabs 15 of the distal flange 6 to an extent that the distal end of the tube 1 and the needle tip 106 can easily penetrate the tympanic membrane in use. The proximal flange 4 advantageously has its final in-use position at which it resists movement through the tympanic membrane, while the distal flange 6 can be easily pushed through because it is retained substantially axially by the fingers 121, the distal flange 6 tabs 15 being pressed radially inwardly.

In more detail, in use the tube 1 is mounted to the device 100 either manually at the point of use or is pre-mounted in the factory. The placement device 100 is moved by the surgeon so that the stem 108 enters the ear canal and the needle tip 106 pierces the tympanic membrane. Advantageously, the face 5 of the proximal flange 4 abuts the tympanic membrane even though the distal flange 6 is folded. This provides an accurate and simple limit to insertion of the stem 108. The tube proximal flange 4 extends radially beyond the distal surface of the sleeve 107, and as it abuts the tympanic membrane, it provides a reference point for visualisation when in use. The proximal flange 4 therefore acts as a limit to insertion, allowing the surgeon to know when the myringotomy knife (needle) 104 has been inserted far enough through the tympanic membrane and to release the tube 1 from the device 100. It is envisaged that, in other embodiments, the sleeve 107 may have a radial dimension which is even smaller relative to that of the proximal flange than illustrated.

Importantly, the fingers 121 radially push the distal flange tabs 15 inwardly so that they can easily pass through the tympanic membrane. However, because the retainer fingers 121 pass through the proximal flange 4 the latter can easily be maintained proximally of the membrane, with its face 5 abutting the membrane and acting as a limiting stop. This allows much more accurate positional control than is the case with prior art devices.

Also, the passageways 10 provide radial retaining strength to the fingers 121, the radially outer surfaces 13 of the passageways 10 pressing the retainer fingers 121 inwardly at a location between the retainer base 122 and their distal ends where they press the distal flange 6 tabs 15 radially inwardly. This helps to ensure that the fingers 121 accurately and reliably retain the distal flange compressed, with the tabs 15 having an axial orientation.

As shown in FIG. 5 the surgeon then operates the deployment mechanism in the handle to cause the needle 104 and the retainer 120 to be retracted in the proximal direction, from the position at which it retains the distal flange tabs 15 radially inwardly to where they allow the tabs to spring out to their natural radial position.

As shown in FIG. 6, the retainer fingers 121 and the needle 104 are attached to each other and so retract together. The sequencing of the retainer and the needle retraction is achieved by the pulling mechanism within the placement device handle.

Figure 7:
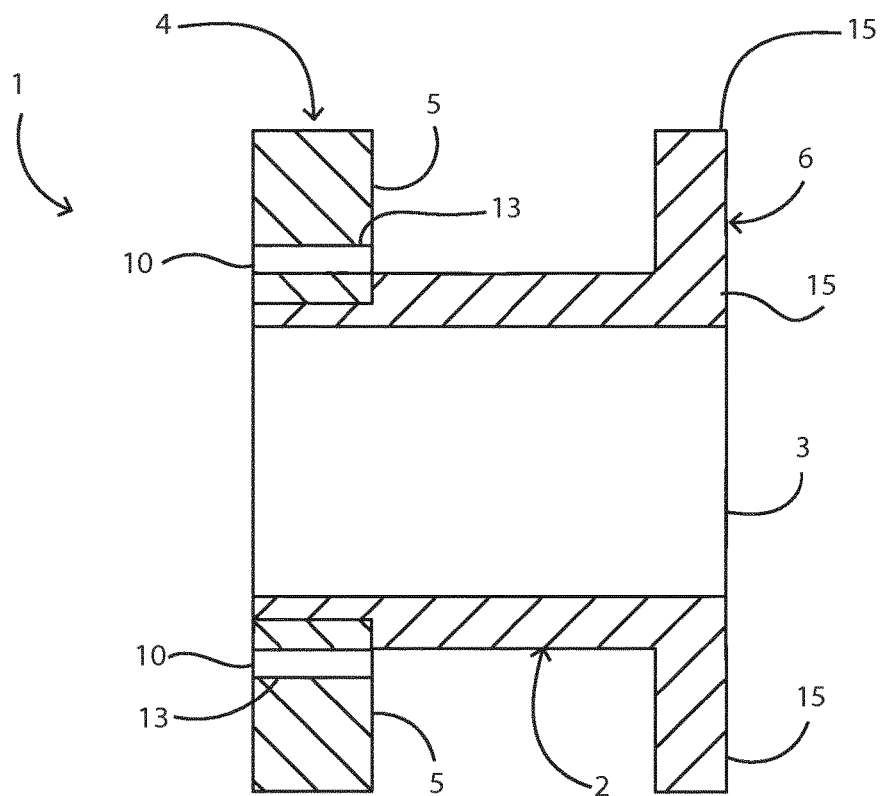
FIG. 7 is a longitudinal sectional view of another tube.

Referring to FIG. 7 a longitudinal sectional view of the tympanostomy tube 1 can be seen. This shows additional detail of the tube, particularly the lumen 3 through the inner flange 6 and the outer flange 4, joined by the inter-flange connector 2. In this particular example, the flange 4 is of a thicker dimension than the flange 6, and the flange 6 comprises the tabs 15 extending outwardly. In this embodiment the proximal flange 4 is of a first rigid material, and the inter-flange connector 2 and the distal flange 6 are integral and of a second, more flexible, material.

The first material is preferably metal such as titanium, and the second material is preferably a material with shape memory properties such as Silicone or Nitinol. This combination of materials allows optimum strength for guiding the retainer fingers and providing structure for the tube during deployment, which prevents the tube from being pulled into the sleeve 107 during deployment, and on the other hand optimum flexibility for the distal flange to fold and release.

Co-moulding is preferably performed for manufacture of the tube where the tube is of different materials to achieve the optimum combination of properties, with rigidity of the proximal flange for guidance of the fingers 121 and acting as a stop, and for the distal flange 6 having an ability to fold over and return to the original radial position quickly and stably. This rigidity of the proximal flange 4 has the added advantage of giving the tube structure during deployment.

In the example of FIGS. 1 to 7, the tube 1 is of a flexible (implant grade silicone) material in the distal flange, and of rigid (titanium, or stainless steel) material in the remainder of the tube. The maximum diameter is 3 mm, and the inter flange distance is 1.6 mm, and the overall length is 2.7 mm in this example. However, the dimensions may be of any suitable combination to suit the clinical requirements.

Figure 8:
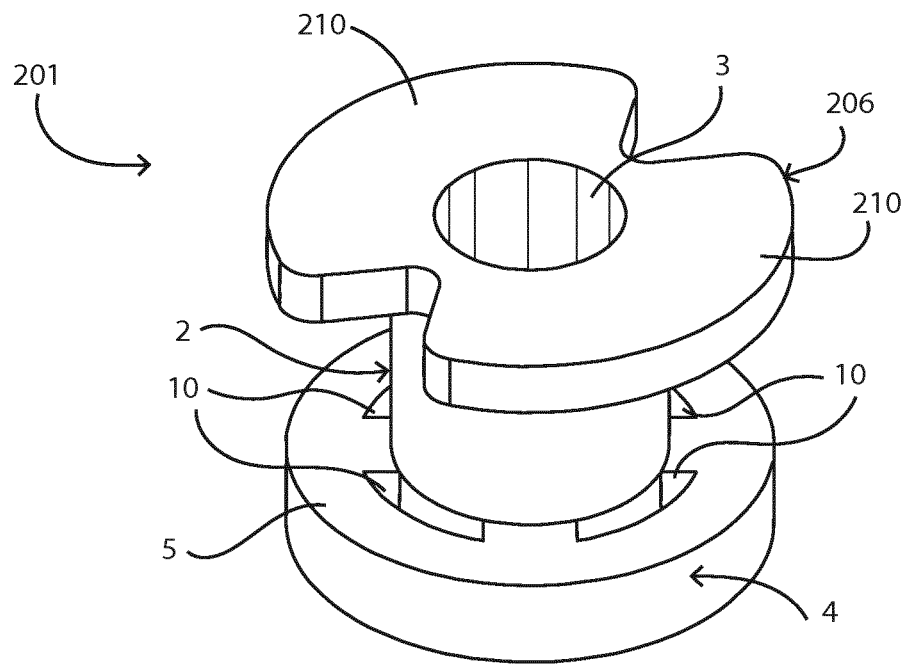
FIGS. 8, 9 and 10 are perspective views of alternative tympanostomy tubes.
Figure 9:
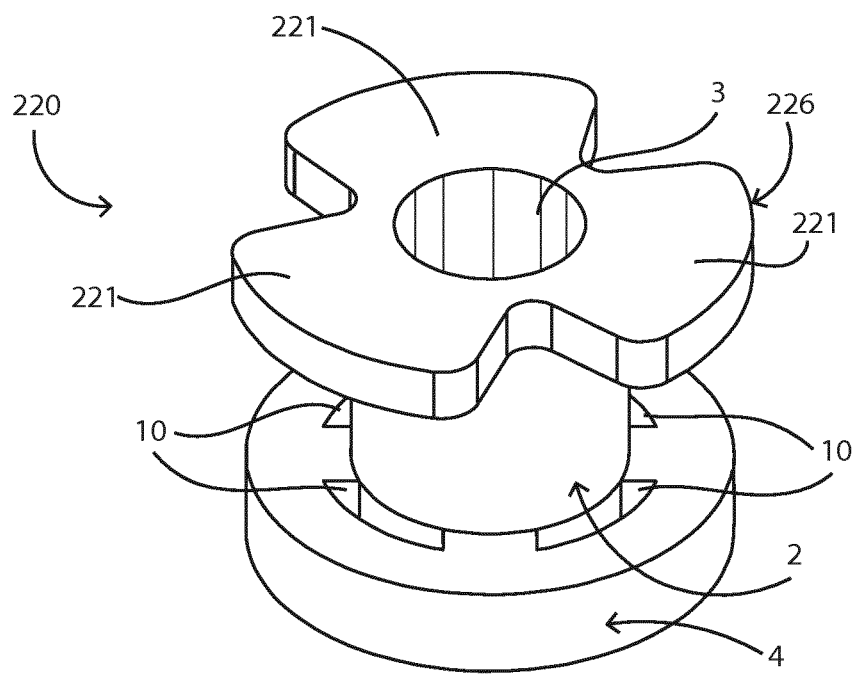
Figure 10:
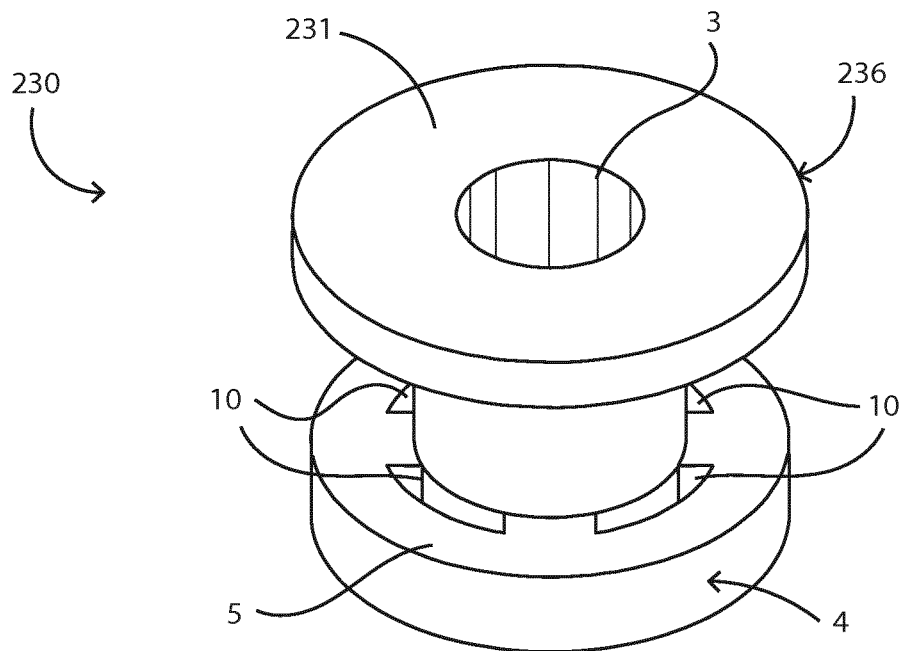

Referring to FIGS. 8, 9, and 10, some alternative embodiments of the tube are shown, in particular in relation to the distal flange. Referring to FIG. 8, a tube 201 is shown with corresponding numerals and parts to the previous embodiment of the tube 1. However, in this embodiment, a distal flange 206 comprises two tabs 210, axially spaced apart by approximately 180°. The passageways of the proximal flange 4 and the device's retainer fingers are correspondingly aligned to match axially the locations of the distal flange tabs 210.

Referring to FIG. 9, a tube 220 is shown with corresponding numerals and parts to the embodiment of the tube 1. However, in this embodiment, a distal flange 226 comprises three tabs 221, axially spaced apart by approximately 120°.

Referring to FIG. 10, a tube 230 is shown with corresponding numerals and parts to the embodiment of the tube 1. However, in this embodiment, a distal flange 236 comprises a single annular body 231. This distal flange 236 has sufficient flexibility to be folded in by a plurality of retainer fingers.

The materials of the tubes 201, 220, and 230 are titanium and silicone.

Figure 11:
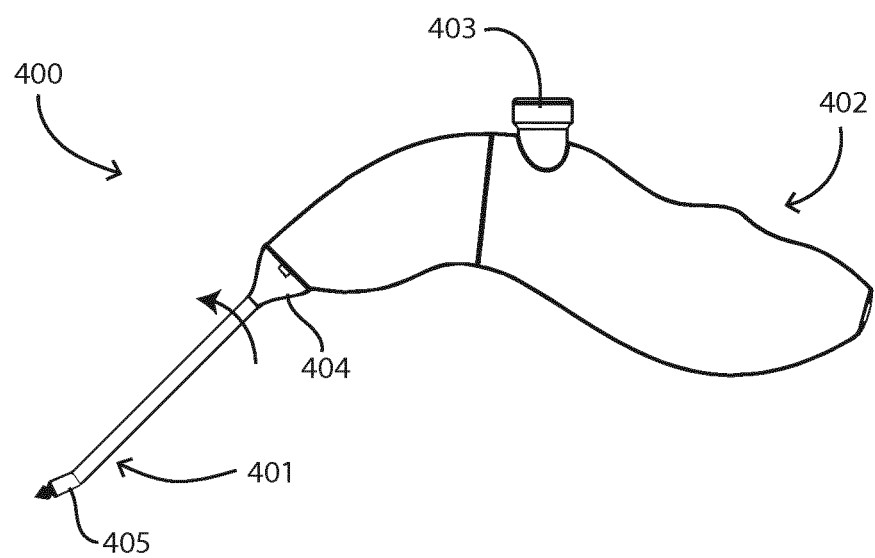
FIG. 11 is a side view of a further placement device.

Referring to FIG. 11 a full placement device 400 has a stem 401, a handle 402, and a user actuator 403. The stem 401 is connected to the handle 402 by a coupler 404 which can be rotated in the direction of the arrow to rotate the stem about its longitudinal axis. The needle stem is in this example flexible. As shown, the distal end of the stem, 405, is angled. Hence, rotation of the stem 401 about its axis allows the tip to be curved in a desired direction to facilitate the hand used by the surgeon and the particular ear being operated upon. A tympanic membrane is often angled to vertical, typically with a slope extending upwardly and outwardly, and furthermore the membrane itself may not be planar, having a conical shape which may not be symmetrical. The coupler 404 and the angle of the stem allows the surgeon to choose an angle which will aid in the tympanic membrane natural angle which can be more acute depending on the anatomy of the person. This angle will allow the tube to be inserted when it is perpendicular to the tympanic membrane. This angle may or may not exist. If it is required, a bend in the stem 401 may be provided to aid better visualisation.

Figure 12:
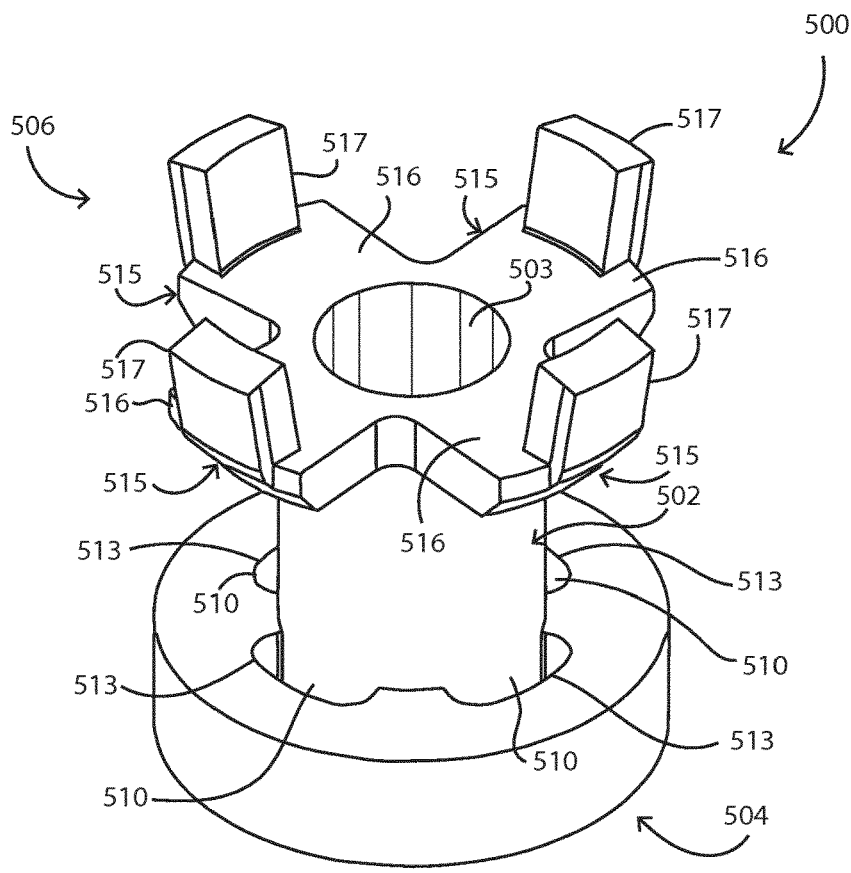
FIG. 12 is a perspective view of an alternative tympanostomy tube.

Referring to FIG. 12 a tympanostomy tube 500 comprises a proximal flange 504, an inter-flange connector 502 with a lumen 503, and a distal flange 506. The proximal flange 504 comprises four axial through-hole passageways 510 at equal 90° separations. The distal flange 506 is configured, as for the other embodiments, to be folded axially to a deployment position and to release radially to a deployed position. Each passageway 510 is adjacent an external surface of the inter-flange connector 502 and each has an arcuate shape with a concave surface 513 facing radially inwardly.

The distal flange 506 has an arrangement of four tabs 515 each having a radial part 516 and an axial part 517. The radial parts 516 extend from the lumen at angle at right angles and more generally preferably +/−30° from radial, and the axial parts 517 each extend from the radial part 516 at an angle of +/−45° from axial.

The tab parts 517 may alternatively be referred to as guide members as their purpose is to assist with guiding of the tube 500 through the tympanic membrane in use by contributing to an arrow shape, as described in detail below.

Figure 13:
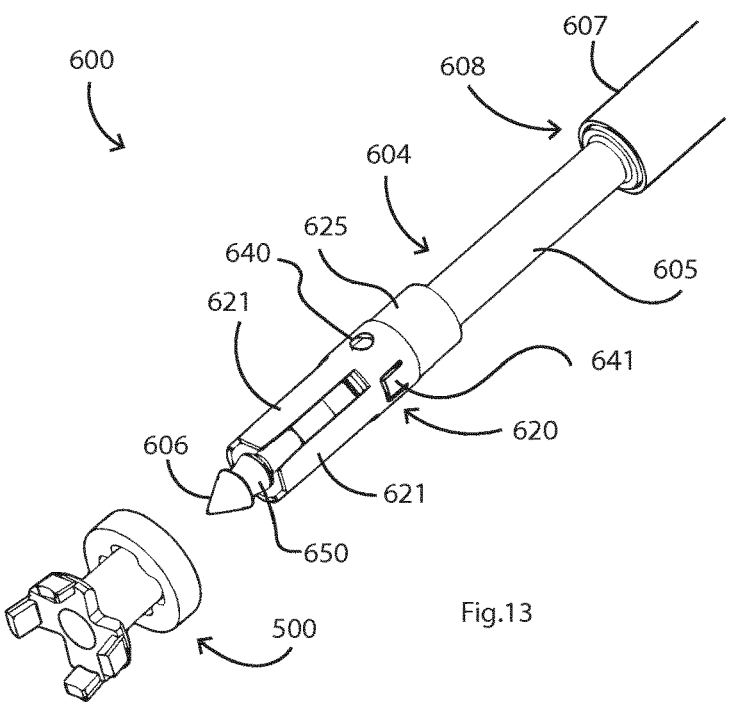
FIG. 13 is a perspective view of an alternative placement device.
Figure 14:
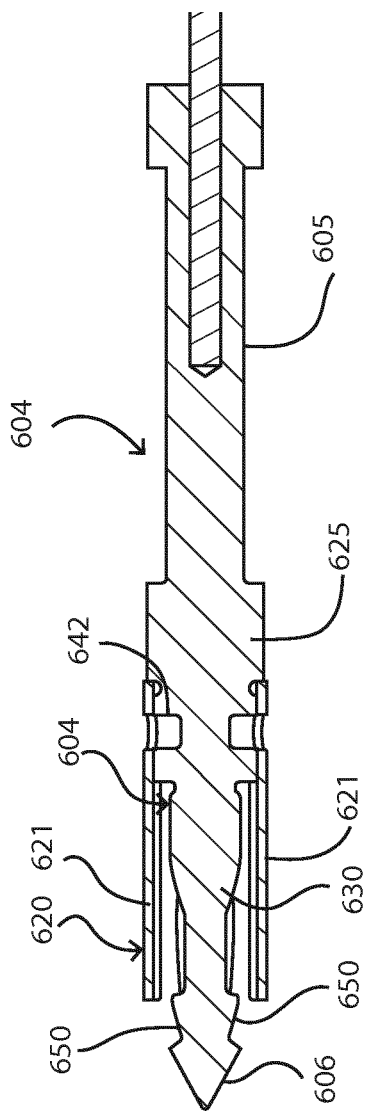
FIG. 14 is a longitudinal sectional view of a distal end of this placement device without a tube and showing particular detail of the needle and retainer.

Referring to FIGS. 13 and 14 a placement device 600 has a stem 608 with a sleeve 607 connected to a deployment mechanism with a handle or having a coupler for connection to such a deployment mechanism.

A needle 604 has a tip 606 configured to pierce a tympanic membrane, the needle having a longitudinal axis Immediately proximally of the tip 606 there is an annular recess 650 having a surface tapered distally and radially inwardly. A retainer 620 comprises four fingers 621 extending axially at a radial distance from the longitudinal axis. The retainer 620 is movable relative to a tube from a pre-deployment distal position at which it is adapted to press radially inwardly against a tube distal flange to retain the distal flange in a folded position, to a deployment proximal position at which the tube distal flange is free to spring out radially to a deployed position.

The fingers 621 have an arcuate cross-sectional shape with a concave internal surface, to fit through the passageways 510.

The retainer 620 comprises an axial guide member 630 configured to fit in the lumen 503 of the tube 500 predeployment. The needle 604 comprises a lock member 625 for engagement within a recess of the stem, not shown. There is a dimple, not shown, in the stem sleeve to secure this engagement.

The retainer 620 is fixed to the needle 604 by a circumferential groove 642 in the needle 604 being engaged by use of a location feature aperture 640 to enable crimping of a clip 641 into the groove 642. This arrangement fixes the retainer 620 to the needle 604. It is envisaged that any outer suitable mechanical and/or adhesive arrangement may be used to ensure that the retainer is fixed to the needle and moves with it during deployment (relative to the tube being deployed).

Figure 15:
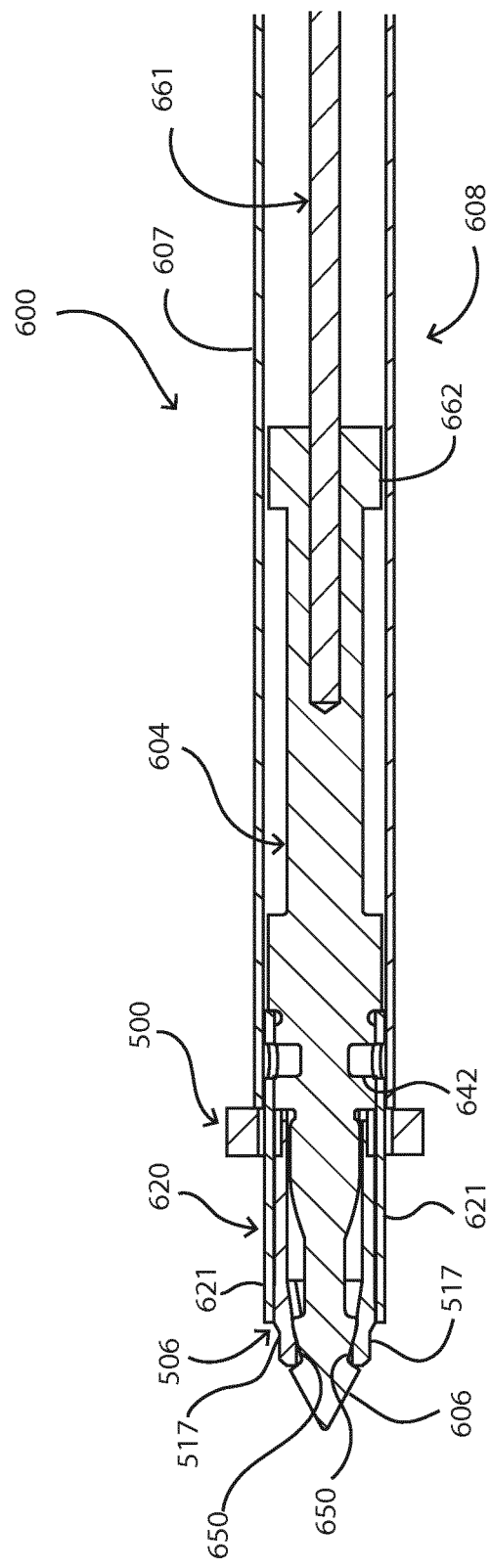
FIGS. 15 to 17 are longitudinal sectional views of the placement device of FIGS. 13 and 14 in use deploying a tube of FIG. 12.
Figure 16:
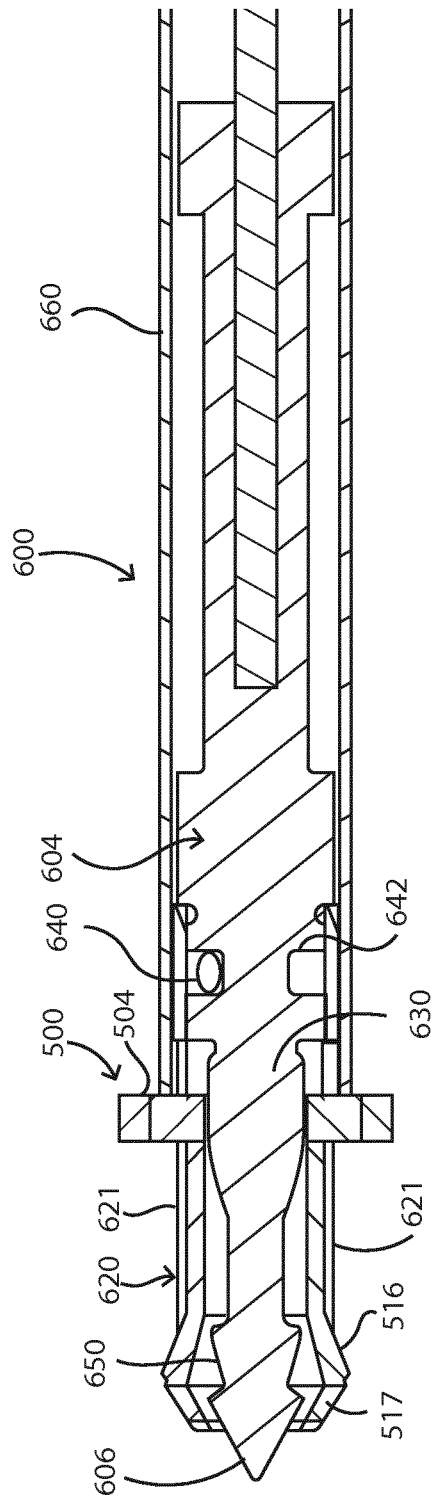
Figure 17:
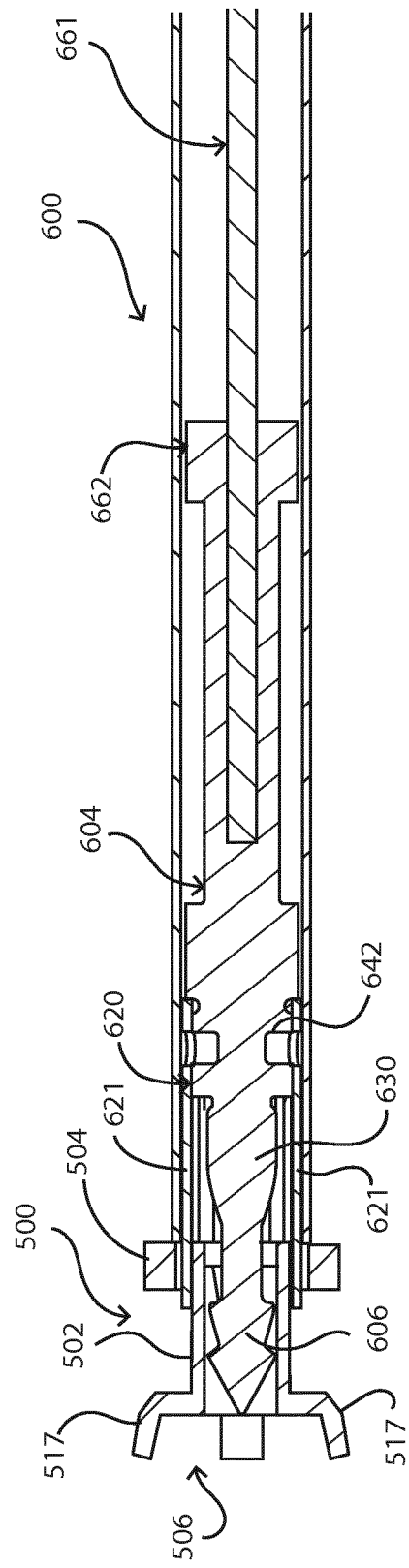

As shown in FIGS. 15 to 17 the placement device 600 has the device stem 608 within which the needle 604 slides according to linear movement of an actuator rod 661 engaged in the needle stem 605. As illustrated, the proximal end of the needle 604 has a flange 662 for sliding engagement at the proximal end while minimising the extent of surface contact between the needle 604 and the internal surface of the stem sleeve 607.

In the pre-deployment situation shown in FIG. 15 the guide parts 517 of the tube 500 distal flange 506 are pressed radially inwardly into the annular recess 650 so that the distal flange 506 effectively forms a continuation of the arrow shape of the needle tip 606. This assists with accurate and effective insertion of the distal flange 506 through the patient's tympanic membrane in a streamlined manner Other benefits of the device 600 are that a lead-in is not required on the tube as it is pre-loaded and has a radial guide to insert the tube while not losing any visualisation of the tube as the proximal flange can be seen at all times as well as working as an end stop when up against the tympanic membrane. These advantages also apply to the earlier embodiments described above.

FIG. 18 shows the overall placement device 600, having a handle 670 with an actuator mechanism. The stem 608 has a bend 680 at its proximal end for improved visualization. The needle 604 is crimped to a cable which links with the actuator in the handle 670.

The invention is not limited to the embodiments described but may be varied in construction and detail. In other examples the retainer fingers have a different cross-sectional shape, such as round, square, or rectangular. The materials of the tube may be different, but it is in general advantageous that the material of the proximal flange be more rigid than that of the distal flange.

As shown by way of example in FIGS. 8 to 10 there may be a different number and position of tabs on the distal flange, and correspondingly different configurations of passageways and retainer fingers. The expected clinical use, especially expected time to extrusion of the tube, will determine these configurations. It is envisaged that the distal flange may not have tabs and indeed may, as shown in FIG. 10, be annular. In such cases there is more requirement that the material of the distal flange be flexible.

It is also envisaged that the proximal flange has passageways which are open in the radial outward direction. This would still provide the benefit of the retainer fingers extending through the proximal flange, and the proximal flange would still have a distally-facing face providing a limiting stop. It is however preferred that the passageways at least have a radially inwardly-facing surface to help retain radial position of the fingers, or that there be a separate inwardly-facing surface on the retainer.

Also, the tube may be made integrally of the same material such as implant grade silicone or other suitable polymer, with the proximal flange being preferably more stiff in its composition. The flange characteristics such as dimension and shape may be modified in order to create a stiff base structure if the composition of the material is not being used in this instance to achieve the required mechanical properties in the proximal flange for the retainer fingers to pass through and to act as a stop against the tympanic membrane in use. An example would be increasing the proximal flange thickness to give the base the rigidity that a co-moulding arrangement would provide by way of the proximal flange being of a stiffer material such as metal. It is also envisaged that the distal end of the stem sleeve may be configured to provide more rigidity to the tube proximal flange, by for example having a greater axially-facing cross-sectional area and/or being of stiffer material such as metal.

The device of the invention may take the form of a cartridge for connection to a third party handle or it may incorporate a handle, preferably with a mechanism for retracting the needle. Also, the mechanism for causing retraction of the needle may be of any desired type, such as for example a conventional actuator for a writing pen.

Also, it is envisaged that the retainer may be movable independently of the needle, retracting to leave the tympanic tube in place, and the needle being withdrawn beforehand or afterwards.

The invention claimed is:

1. A tympanostomy tube placement device comprising:
a stem connected to a deployment mechanism or having a coupler for connection to a deployment mechanism;
a needle having a tip configured to pierce a tympanic membrane, the needle having a longitudinal axis; and
a retainer comprising a plurality of fingers extending axially at a distance from said longitudinal axis;
wherein the retainer is movable from a pre-deployment distal position at which it is adapted to press radially inwardly against a tube distal flange to retain said distal flange in a folded position, to a deployment proximal position at which a tube distal flange is free to spring out radially to a deployed position;
a handle connected to the stem, and the stem being rotatable with respect to the handle; and
a user actuator for rotation of the stem, and wherein the needle is lockable in the stem so that the needle rotates with the stem.

2. The placement device as claimed in claim 1, wherein there are at least two diametrically opposed retainer fingers.

3. The placement device as claimed in claim 1, wherein the fingers have an arcuate cross-sectional shape with a concave internal surface.

4. A tympanostomy tube placement device comprising:
a stem connected to a deployment mechanism or having a coupler for connection to a deployment mechanism;
a needle having a tip configured to pierce a tympanic membrane, the needle having a longitudinal axis; and
a retainer comprising a plurality of fingers extending axially at a distance from said longitudinal axis;
wherein the retainer is movable from a pre-deployment distal position at which it is adapted to press radially inwardly against a tube distal flange to retain said distal flange in a folded position, to a deployment proximal position at which a tube distal flange is free to spring out radially to a deployed position;
a tympanostomy tube comprising a proximal flange, an inter-lumen connector, and a distal flange, and in which the proximal flange comprises passageways; and in which
in a pre-deployment position the retainer fingers extend through the proximal flange passageways and press the tube distal flange inwardly;
wherein the tube distal flange includes a plurality of tabs aligned in circumferential position with a retainer finger and being pressed inwardly by said finger in the pre-deployed position, and wherein there are four tabs, spaced apart by approximately 90°.

5. The placement device as claimed in claim 4, wherein the passageways are through holes, each having a surface facing radially inwardly and engaging an outer surface of a the retainer finger.

6. The placement device as claimed in claim 4, wherein the passageways are through holes, each having a surface facing radially inwardly and engaging an outer surface of a the retainer finger; and wherein at least one through hole has an arcuate shape and said surface is concave.

7. The placement device as claimed in claim 4, wherein the tube proximal flange is of a first material and the distal flange is of a second material, and said first material is more rigid than the second material.

8. The placement device as claimed in claim 4, wherein the retainer or the needle comprise an axial guide member configured to fit in the lumen of the tube pre-deployment.

9. The placement device as claimed in claim 4, wherein the needle comprises a recess proximally of the tip and configured to receive a folded-down part of a tab of a the tube distal flange.

10. The placement device as claimed in claim 4, wherein the needle and the tube distal flange are configured to form an arrow-shaped formation when the distal flange is folded down.

11. A tympanostomy tube placement device comprising:
- a stem connected to a deployment mechanism or having a coupler for connection to a deployment mechanism;
- a needle having a tip configured to pierce a tympanic membrane, the needle having a longitudinal axis; and
- a retainer comprising a plurality of fingers extending axially at a distance from said longitudinal axis;
- wherein the retainer is movable from a pre-deployment distal position at which it is adapted to press radially inwardly against a tube distal flange to retain said distal flange in a folded position, to a deployment proximal position at which a tube distal flange is free to spring out radially to a deployed position;
- a tympanostomy tube comprising a proximal flange, an inter-lumen connector, and a distal flange, and in which the proximal flange comprises passageways; and in which
- in a pre-deployment position the retainer fingers extend through the proximal flange passageways and press the tube distal flange inwardly;
- wherein the needle comprises a recess proximally of the tip and configured to receive a folded-down part of a tab of the tube distal flange.

12. The placement device as claimed in claim 11, wherein the tube distal flange comprises at least one tab aligned in circumferential position with a retainer finger and being pressed inwardly by said finger in the pre-deployed position.

13. The placement device as claimed in claim 11, wherein the tube distal flange comprises a plurality of tabs aligned in circumferential position with a retainer finger and being pressed inwardly by said finger in the pre-deployed position.

14. The placement device as claimed in claim 11, wherein the tube distal flange comprises a plurality of tabs aligned in circumferential position with a retainer finger and being pressed inwardly by said finger in the pre-deployed position, and wherein the tabs are substantially equally circumferentially spaced.

15. The placement device as claimed in claim 11, wherein the tube distal flange comprises a plurality of tabs aligned in circumferential position with a retainer finger and being pressed inwardly by said finger in the pre-deployed position; and wherein there are four tabs, spaced apart by approximately 90°.

16. The placement device as claimed in claim 11, wherein the passageways are through holes, each having a surface facing radially inwardly and engaging an outer surface of a retainer finger.

17. The placement device as claimed in claim 11, wherein the passageways are through holes, each having a surface facing radially inwardly and engaging an outer surface of a retainer finger; and wherein at least one through hole has an arcuate shape and said surface is concave.

18. The placement device as claimed in claim 11, wherein the tube proximal flange is of a first material and the distal flange is of a second material, and said first material is more rigid than the second material.

19. The placement device as claimed in claim 11, wherein the retainer or the needle comprise an axial guide member configured to fit in the lumen of the tube pre- deployment.

20. The placement device as claimed in claim 11, wherein the needle and the tube distal flange are configured to form an arrow-shaped formation when the distal flange is folded down.

* * * * *